United States Patent
Sudarev et al.

(10) Patent No.: US 9,265,693 B2
(45) Date of Patent: Feb. 23, 2016

(54) METHOD AND DEVICES PROVIDING IMPACT ON CARDIOVASCULAR SYSTEM

(76) Inventors: Aleksey Monesovich Sudarev, Moscow (RU); Evgeny Vladimirovich Korotich, Murmansk (RU)

(*) Notice: Subject to any disclaimer, the term of this patent is extended or adjusted under 35 U.S.C. 154(b) by 580 days.

(21) Appl. No.: 13/699,880

(22) PCT Filed: Jul. 5, 2011

(86) PCT No.: PCT/RU2011/000487
§ 371 (c)(1),
(2), (4) Date: Nov. 26, 2012

(87) PCT Pub. No.: WO2012/005630
PCT Pub. Date: Jan. 12, 2012

(65) Prior Publication Data
US 2013/0102939 A1    Apr. 25, 2013

(30) Foreign Application Priority Data

Jul. 6, 2010 (RU) .................................. 2010127469
Jul. 27, 2010 (RU) .................................. 2010131388

(51) Int. Cl.
| A61H 31/00 | (2006.01) |
|---|---|
| A61H 9/00 | (2006.01) |
| A61B 5/0225 | (2006.01) |
| A61B 5/0456 | (2006.01) |
| A61B 5/00 | (2006.01) |
| A61M 1/10 | (2006.01) |
| A61B 5/1455 | (2006.01) |

(52) U.S. Cl.
CPC ............ *A61H 31/004* (2013.01); *A61B 5/0225* (2013.01); *A61B 5/0456* (2013.01); *A61B 5/7285* (2013.01); *A61H 9/0078* (2013.01); *A61M 1/107* (2013.01); *A61B 5/14551* (2013.01); *A61H 2201/5002* (2013.01); *A61H 2201/5015* (2013.01); *A61H 2201/5071* (2013.01); *A61H 2205/06* (2013.01); *A61H 2205/083* (2013.01); *A61H 2205/10* (2013.01); *A61H 2230/045* (2013.01); *A61H 2230/208* (2013.01); *A61H 2230/255* (2013.01); *A61H 2230/305* (2013.01); *A61H 2230/505* (2013.01)

(58) Field of Classification Search
CPC ... A61H 9/0078; A61H 9/0092; A61H 31/00; A61H 31/004; A61H 31/005; A61H 31/006; A61H 2230/045
See application file for complete search history.

(56) References Cited

U.S. PATENT DOCUMENTS

| 3,835,845 | A | * | 9/1974 | Maher | ................. | A61B 5/0285 601/150 |
|---|---|---|---|---|---|---|
| 4,077,402 | A | * | 3/1978 | Benjamin, Jr. | ....... | A61B 5/0285 601/150 |
| 4,753,226 | A | * | 6/1988 | Zheng | ................. | A61H 9/0078 601/150 |
| 7,048,702 | B2 | * | 5/2006 | Hui | ...................... | A61H 9/0078 601/150 |
| 2003/0144690 | A1 | * | 7/2003 | Zheng | ................. | A61B 5/0535 606/201 |
| 2005/0075531 | A1 | * | 4/2005 | Loeb | .................... | A61H 9/0078 600/17 |
| 2005/0126578 | A1 | * | 6/2005 | Garrison | ............. | A61H 9/0078 128/874 |

(Continued)

*Primary Examiner* — Valerie L Skorupa
(74) *Attorney, Agent, or Firm* — Aleksandr Smushkovich

(57) ABSTRACT

The proposed method and devices provide for an effective improvement of the blood flow in the vessels of a human's extremities due to generation of an ante-grade pressure wave of blood synchronized with phases of the cardiac cycle with the help of compression impulses. The devices provide an improved accuracy of the time and amplitude characteristics of the compression impulses and functioning in modes of generation both the ante-grade wave and external counter-pulsation.

13 Claims, 9 Drawing Sheets

(56) References Cited

U.S. PATENT DOCUMENTS

| | | | |
|---|---|---|---|
| 2006/0004245 A1* | 1/2006 | Pickett | A61H 9/0078 600/16 |
| 2006/0058717 A1* | 3/2006 | Hui | A61H 9/0078 601/152 |
| 2008/0033228 A1* | 2/2008 | Rastegar | A61H 9/0078 600/16 |

* cited by examiner

METHOD AND DEVICES PROVIDING IMPACT ON CARDIOVASCULAR SYSTEM

CROSS-REFERENCE TO RELATED APPLICATIONS

This application is a U.S. national stage application of a PCT application PCT/RU2011/000487 filed on 12 Jan. 2012, whose disclosure is incorporated herein in its entirety by reference, which PCT application claims priority of a patent application RU2010127469 filed on 6 Jul. 2010, and of a patent application RU2010131388 filed on 27 Jul. 2010.

FIELD OF THE INVENTION

The present invention concerns medicine and medical devices and may be used for treatment and prevention of cardiovascular diseases as well as for training the endurance at physical exercises.

BACKGROUND OF THE INVENTION

Diseases of the cardiovascular system and vessels of the limbs, including obliterating atherosclerosis, endarteritis, and diabetic angiopathy are the forms of severe pathology; their treatment commonly is limited to administration of various pharmacological agents (Charles F. Carey etc. "The Washington manual of medical therapeutics"). Non-medicamentous management of the diseases and devices used for this are also known. The methods are based on rhythmic pneumatic compression of the vessels of an affected extremity synchronized with the cardiac activity, so called "syncardiac" massage. As an example, the "Syncardon" device and similar appliances include an ECG registration system and a cuff which should be put to a limb; the cuff is attached to a pneumatic system for achieving compression with air waves of a variable pressure synchronized with ECG signals (see U.S. Pat. No. 4,077,402, Benjamin et al., Jul. 3, 1978; SU712085, Khapilov et al., Jan. 30, 1980; SU986421, Solovyev et al., Jul. 1, 1983).

There is a method of treatment for vascular diseases of the lower extremities consisting of ECG monitoring of the patient and generating sequences of the pressure impulses within a compression element placed over the affected extremity, where the impulses of the pressure are synchronized with QRS-complex parameters of the ECG (see patent U.S. Pat. No. 5,514,079, Dillon, Jul. 5, 1996). Impulse parameters of the pressure and its duration are chosen in order that the impulse is generated with a delay in relation to QRS-complex, and the descending part of the impulse is finished prior to initiation of the systole of the QRS-complex. The device includes an ECG analyzer connected to a computer which is attached to the driving point of the control and indication unit a driving output of which is attached to a compression element via gas distribution device and a source of the compressed air. The compression element provides loading along all the extremity from the foot up to the knee. A disadvantage of the method is the limited functional capacity which prevents selectivity of the impact that doesn't allow creating an effective antegrade wave of the blood pressure. It is known about the use of independently managed compressive cuffs which are usually placed to proximal and distal parts of an affected extremity for creation of the antegrade wave of the blood pressure, but this method is used without synchronization with QRS-complexes (RU2253429 C1, Amosov et al., Oct. 6, 2005) that reduces the efficacy of such an impact.

There is a device for performing external counterpulsation which is synchronized with the cardiac rhythm (RU2135216 C1, Vasomedical Inc, Aug. 27, 1999). This device contains a source of a compressed gas, e.g. an air compressor with the maximum pressure up to 0.2 MPa, a positive pressure receiver, a negative pressure receiver, and gas-distributing components attached to compression cuffs. The device also contains a control unit for duration of filling/emptying of the cuffs, an analyzer of the ECG, ABP, blood oxygen saturation ($SpO_2$) parameters, and a unit of visualization of the measured and managed parameters.

There is a device containing a source of the compressed air connected via a receiver to a limiter of pressure and gas-distribution units which are connected with occlusive compression cuffs placed on the patient's body and supplied by pressure sensors, a unit for measurements of the cardiovascular system parameters connected to a control and indication unit (RU2282465 C2, Sudarev et al., Aug. 27, 2006). The main disadvantage of the device is a need of the use of a high-pressure compressor that increases considerably power consumption and mass-dimensional characteristics of the device.

A device (WO2007008201 (A1), Pickett et al., Jan. 18, 2007), contains a source of compressed air, a positive pressure receiver, gas-distributing units connected to compression cuffs, a source of the high pressure (minicompressor) controlling the valves of a gas-distributing unit; a valve assuring pressure release from the receiver. The device also contains a pressure sensor, a control unit for valves of the gas-distributing unit, an analyzer of the ECG, and a visualization unit of the parameters measured and managed. However, it is not capable of separate managing the pressure impulse magnitude in the compression cuffs that is rational in case of any changes of patient's physiological parameters.

SUMMARY OF THE INVENTION

The present invention is designed to enhance the effective impact on the human's cardiovascular system and treatment and prevention of the cardiovascular diseases and vascular pathologies of the limbs (extremities), including the obliterating endarteritis, obliterating atherosclerosis, diabetic angiopathy, etc. The patent-pending devices are designed to enhance the functional capabilities: they allow providing both external a counterpulsation mode and a mode of the antegrade wave of impact directed mainly to the arterial segment of the vascular system of a human's limbs.

In accordance to the present invention, the inventive method of impact on the cardiovascular system includes a periodical compression of the limbs with pressure impulses synchronized with a QRS-complex of ECG according to parameters of a blood flow pulse wave and correction of the impulse parameters based on a registered blood flow measured distal to the compression area.

The inventive method is characterized by compression of each affected extremity performed separately in two areas, proximal and distal, impulses to which are delivered with a delay in relation to each other;

Within the proximal area, the onset of the pressure impulse is delayed in relation to the R-peak of the current QRS complex so that the impulse in a proximal cuff would start on coming of the pulse wave from the heart to the mentioned proximal area.

Within the distal area, the onset of the pressure impulse in relation to the onset of the pressure impulse in the said proximal area is delayed for the time of transmission of the pulse wave from one area to another one. Meanwhile, compression within the said proximal and distal areas is stopped simultaneously until the onset of the following QRS complex.

According to another subject-matter the device impacting the cardiovascular system includes a means for creation of periodical compression of an extremity connected with a source of compressed air via a gas-distribution unit; a control and indication unit connected with a gas-distribution unit, with an analyzer of ECG QRS-complex, and with a unit for registration of the blood flow in the limb.

The control and indication unit is capable of control of sending pressure impulses into the said cuffs with a delay in relation to the R-peak of the current QRS-complex so that the onset of the impulse in a proximal cuff would correspond to the period of the pulse wave transmission from the heart to the site of application of the said proximal cuff.

The magnitude of the onset delay for the pressure impulse in the distal cuff in relation to the beginning of the pressure impulse in the proximal cuff complies with the transmission time of the impulse wave between the cuffs. Cut-off point for termination of the pressure impulses in the proximal and distal cuffs is the same and its onset is earlier than the beginning of the following QRS complex.

The device may contain cuffs for each limb: the arm, forearm, thigh, and the shin (calf); these cuffs are connected to gas-distribution units with corresponding cuffs in a parallel way.

According to another subject matter, the device impacting the cardiovascular system includes compression cuffs, attached to the patient's body and attached to a source of compression air via gas-distributing units and a receiver; a source of high pressure, sensor of pressure in the compression cuffs, a QRS-complex analyzer (based on ECG) and a plethysmographic registration device connected with a control and indication unit, a receiver of the negative pressure. Each gas-distribution unit contains two pneumatic mechanical quick exhaust air valves, four electromechanical distributors and the pressure sensor. Control inputs of the pneumatic mechanical quick exhaust air valves are connected to a source of high pressure by means of electromechanical distributors; the output of one of the pneumatic mechanical quick exhaust air valves is attached to a corresponding compression cuff, and the output of another one is attached to a negative pressure receiver. The control and indication unit may have the upper and lower control circuits. The upper control circuit is produced based on a personal computer capable of analysis of physiological signals reflecting the patient's condition and capable of sending control instructions to the lower control circuit represented in the form of a microprocessor-based controller for generation of control signals to gas-distribution units.

The technical result consists of producing an effective antegrade pressure wave along the vessels synchronized with phases of the cardiac cycle. The patent-pending aggregate of attributes of the devices provides enhancement of accuracy of time characteristics generation of pneumatic impulses in relation to parameters of the QRS-complex for production of an effective antegrade blood pressure wave which is directed to an increment of the blood flow in the distal regions of extremities as well as the universality of generation of impact modes.

Other peculiarities of the invention will be clarified on the basis of a detailed description below.

BRIEF DESCRIPTION OF THE DRAWINGS

The concept of the invention is explained in the drawings wherein.

DETAILED DESCRIPTION OF THE INVENTION

Figure 1:
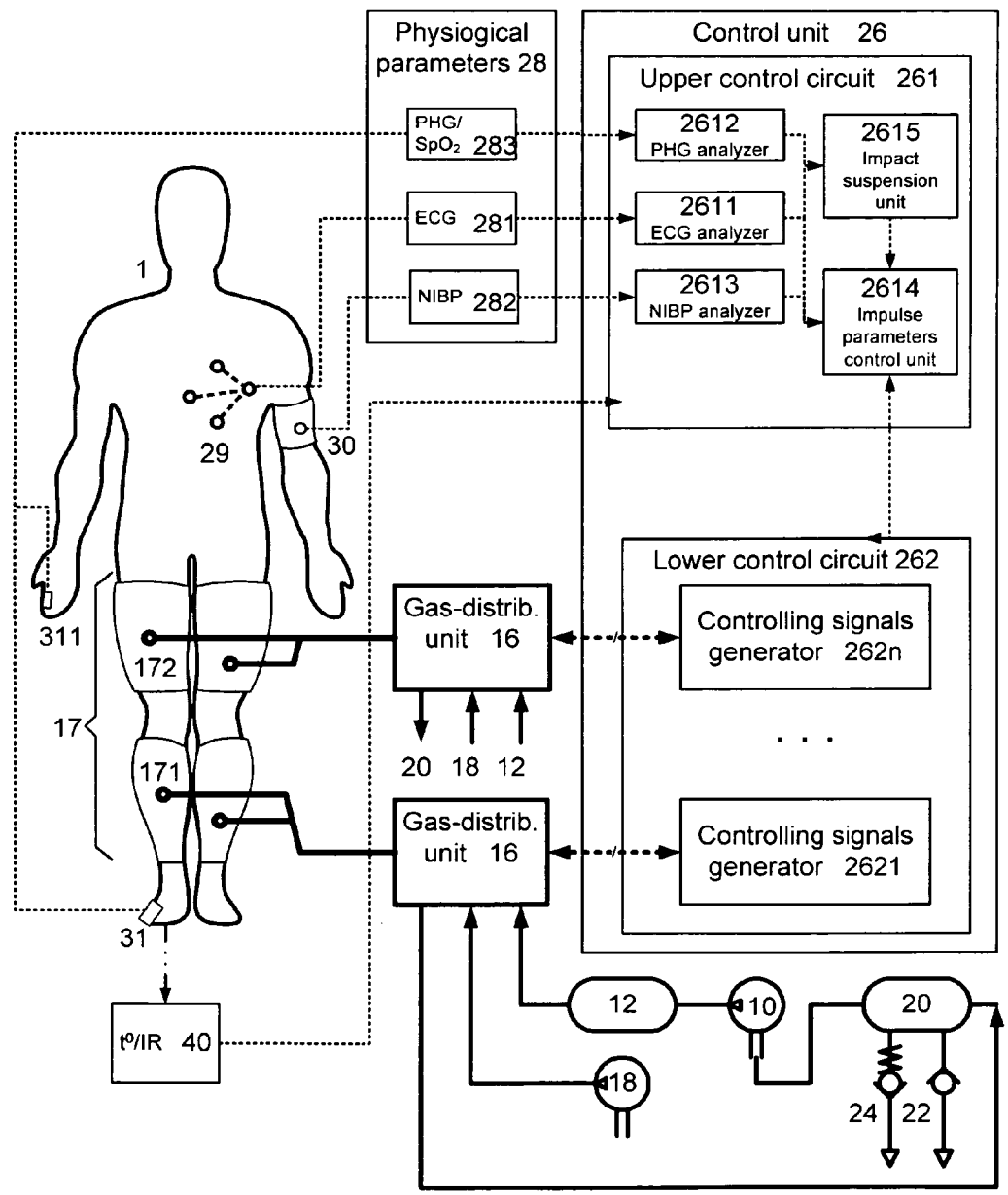
FIG. 1: demonstrates a block diagram of the inventive device.

While the invention may be susceptible to embodiment in different forms, there are shown in the drawings, and will be described in detail herein, specific embodiments of the present invention, with the understanding that the present disclosure is to be considered an exemplification of the principles of the invention, and is not intended to limit the invention to that as illustrated and described herein.

The present method produces an antegrade blood flow wave in vascular diseases of the extremities by means of cardiac rate synchronized generation of pressure impulses in the compression cuffs placed over the extremity.

For this, the following parameters must be determined:
a) duration of the delay between the R-peak (also called 'R-wave') of the QRS-complex and the beginning (rising edge) of the pressure impulse in the compression cuff placed over a proximal region;
b) duration of the delay between the pressure impulses in the compression cuffs placed over the proximal and distal regions.

A too short duration of the front edge of the pump pressure impulse increment as well as not long duration of compression produces a high perfusion pressure in the distal regions. It leads to a substantial increase of the blood flow in the regions. Furthermore, the recommended modes of synchronization of the antegrade pressure wave generated at compression with the natural pressure wave improve the efficacy of pressure wave due to superposition of the waves. Any peripheral pulse wave below the area of compression is the superposition of these two waves. The first wave is the pulse wave associated with the cardiac contraction, and the second wave is associated with sequential compression.

Like the effects generated at sequential external counterpulsation, a reinforced antegrade pressure wave increases the blood flow velocity and shearing stress in the blood vessels.

In contrast to the sequential external counterpulsation, these effects become evident mainly in the vessels of the limbs located distal to the region being impacted. Respectively, such a hemodynamic effect produces an analogous positive change in the distal regions influencing the endothelium of vessels of the lower extremities.

It leads to opening of additional vessels in the circulation due to secretion of vasodilating factors and to an increase of synthesis of vascular growth factors (factors of angiogenesis) in the extremities.

Implementation of method being claimed may be easily explained by an example of action of the device for impacting the cardiovascular system which may function in two main modes: a) the impact on the arterial segment of the limb vascular system; b) external counterpulsation.

A flowchart diagram of the inventive device for producing an impact on the cardiovascular system of a human is demonstrated in the FIG. 1. Pneumatic connections are drawn with a solid line, and electrical links are drawn with a dotted line. A patient is designated at position 1.

The device comprises: a source 10 of compressed air, e.g. a compressor of the Becker manufacturer (the model DT 4.40) with a built-in regulator-limiter of output pressure, a receiver 12, gas-distribution units 16 according to a number of independent groups of compression cuffs 17, a source 18 of high pressure, e.g. a compressor of the Thomas manufacturer (the model 7006), a receiver 20 of negative pressure. Both a non-return spring-assisted valve 24 for creation of a negative pressure level in the receiver 20 and a valve 22 used for quick pressure release from the receiver 20 into the environment, are connected to the receiver 20.

The inventive device comprises a control and indication unit 26 and an associated unit 28 used for measurements of the patient's physiological parameters. The unit 28 is connected to electrodes 29 positioned on the patient's body and used for registration of the ECG, to a compression cuff 30 of the blood pressure measurer, a digital sensor 31 or 311, e.g. taken from a pulse oximeter for registration of plethysmograph.

The unit 28 contains an ECG analyzer 281, and a blood pressure measurer 282, a device for plethysmogram measurement 283, e.g. a pulse oximeter, outputs of which are connected to the unit 26 with the use of standard interfaces, e.g. USB.

To control the efficacy and duration of periodical compression procedure a device 40 united with a unit 26 for registration of temperature in the peripheral parts of affected extremity was developed. This may be done, e.g. in the form of thermistor, attached to the peripheral area of an affected extremity (to a finger or toe) or in the form of a contactless appliance for measurement and analysis of the temperature spatial distribution, e.g. computer-assisted thermographic recorder.

Figure 2:
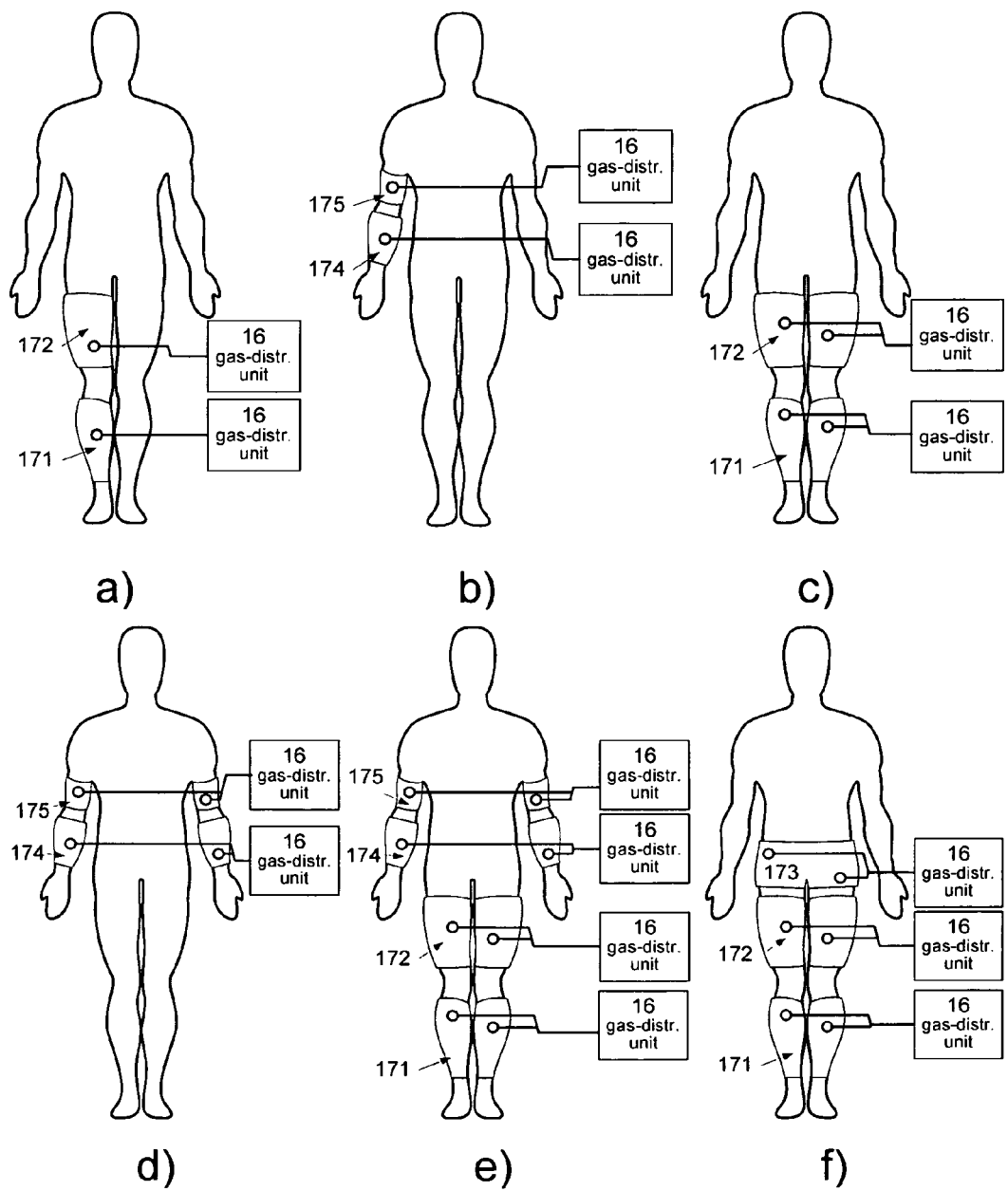
FIG. 2: illustrates layout charts of sensors and compression cuffs on the patient's body.

FIG. 1 shows one of the possible configurations of superposition of compression cuffs 17 applied to the patient 1: two cuffs 171 on the calves and two cuffs 172 on the thigh are put over the lower extremity; these are connected to suitable gas-distribution units 16 (other configurations are shown in the FIG. 2).

The unit 26 is equipped with a two-level control circuit, including: an upper control circuit 261 is designed for instance on the basis of a personal computer capable of analysis of the physiological signals concerning the patient's condition and a lower control circuit 262 receiving commands generated by the upper control circuit 261. The circuits 261, 262 are connected to each other by means of a double-sided digital communication interface for data exchange and management.

The upper control circuit 261 comprises:

A unit 2611 for ECG analysis. It provides real-time estimation of the following amplitude-time parameters of the ECG: periods of QRS-complexes, points of R-peaks, duration of RR-intervals, and the cardiac rate. Furthermore, it is used for the analysis of the heart rate variability based on amplitude-time analysis of the ECG parameters recorded during the procedure.

A unit 2612 for analysis of the plethysmographic signals. It provides a real-time analysis of the shape and determination of the amplitude-time parameters of a plethysmogram. Furthermore, while the plethysmogram registration device 283 and a corresponding sensor 31 or 311 are the parts of a pulse oxymeter, the unit 2612 additionally performs the analysis of blood oxygen saturation ($SpO_2$).

A unit 2613 for analysis of the arterial blood pressure parameters. During the procedure, it provides periodical measurements of blood pressure parameters, in particular, the level of systolic blood pressure.

A unit 2614 for synchronization and control for the amplitude-time characteristics of compression impulses in the cuffs 17. Depending on the amount n of independent groups of cuffs 17, the unit 2614 produces commands for the lower control circuit 262 synchronized with ECG signals, particularly with the time point of the last R-peak. Furthermore, it manages delays of the start and stop of the pressure impulses in each of the independent group of the cuffs 17 in relation to the R-peaks of the ECG. Moreover, depending on the physiological parameters received from the units 2612, 2613 (the systolic blood pressure value, the forms of plethysmogram), the unit 2614 makes corrections for parameters of compression pressure in the cuffs 17.

A unit 2615 of impact suspension in case of receiving of the values of the physiological parameters that exceed predetermined borderline values from the analytical units 2611 to 2613.

A lower circuit 262 is designed in the form of a microprocessor-based controller for generation of controlling signals for gas-distributing units 16, and it contains generators 2621 ... 262n of controlling signals that correspond the number n of the units 16.

Each of the gas-distribution units 16 (FIG. 8) comprises: electromechanical distributors 161 and 162 for managing pneumatic mechanical quick exhaust air valves 165 for pressure pumping into a cuff, electromechanical distributors 163 and 164 to control pneumatic mechanical quick exhaust air valve 167 for pressure release from the cuff, a pressure sensor 166 in the cuff. The inlet of valve 165 is connected with the source 10 via the receiver 12. The controlling pneumatic inlet of valve 165 is connected to a pneumatic outlet of the distributor 161, the pneumatic outlet of which is connected to the negative pressure receiver 20 or with the atmosphere (environment), and with the pneumatic outlet of distributor 162, the pneumatic inlet of which is connected to the source of high pressure 18. The pneumatic outlet of device 165 is connected to a corresponding compression cuff.

In turn, the pneumatic inlet of valve 167 is connected to a corresponding compression cuff; the controlling pneumatic inlet is connected to the pneumatic outlet of distributor 163, the pneumatic inlet of which is connected to the high pressure source 18, and with the pneumatic outlet of distributor 164, the pneumatic inlet of which is connected to the receiver 20 of negative pressure.

To decrease the consumption of air from the source 18, instead of the high pressure source 18 it is possible to supply compressed air to the inlet of distributor 163 from the receiver 12.

The pneumatic outlet of valve 167 is connected to the input of the receiver 20. The pneumatic inlet of pressure sensor 166 is connected to a corresponding compression cuff, and the electrical output as well as electrical inputs of distributors 161 to 164, are connected to the control and indication unit 26.

a) Functioning in a Mode of Impact on the Arterial Segment of the Vascular System of Limbs:

The device produces an antegrade blood flow wave as follows.

As it is demonstrated in the FIGS. 2,*a-e*, the compression cuffs 17 are put over one or several extremities of the patient 1, and the electrodes 29 for ECG registration, the compression cuff 30 for measurement of blood pressure, and the finger sensor 31 or 311 for plethysmogram registration are attached. The sensor 31 is placed over a distal part e.g. a finger or toe of the extremity to which a periodical compression exposure is provided. Then, power supply of the sources 10 and 18 is connected to the units 26, 28.

The unit 26 provides analysis and visualization of the physiological signals received from the unit 28: registered with ECG analyzer 281, the blood pressure measurer 282, and the device for plethysmogram registration 283. Information gathered due to measurements and analysis is represented on the computer's screen that allows a physician to choose a mode of impact.

The unit 26 is capable of control for sending pressure impulses to independent groups of cuffs 17 with various delays in relation to R-peaks of the current QRS-complex of ECG. In the distal cuff, for instance in the cuff 171, placed over the calf, the beginning of the pressure impulse in relation to the beginning of the pressure impulse in the proximal cuff 172 placed over the thigh is delayed for the transmission time of the pulse wave between cuffs 172 and 171. Sending pressure impulses to the cuffs is stopped simultaneously prior to initiation of the following QRS-complex.

The method, implemented with the use of the inventive device may be performed with several pairs of simultaneously functioning compression cuffs (placed to the thigh and calf, to the arm and the forearm of each extremity) connected to gas-distribution units 16 with the corresponding cuffs in a parallel way (see FIG. 2). The values of impulse pressures are set with an excess of the systolic pressure in the arteries of extremities, mainly by 10 to 50 mm Hg that provides complete occlusion of vessels of the extremities.

The values of impulse pressures in the distal area of the compression are set below the values of pressure impulses assigned for the proximal area of the compression, mainly by 10 to 40 mm Hg. Such a mode guarantees occlusion of the distal area. Such a mode is capable of providing compression of the vessels of the distal area and creation of the antegrade pressure wave.

The onset of pressure impulses in the proximal area of compression (cuff 172) in relation to R-peak of the current QRS-complex is delayed by the value $t_1$ calculated on the basis of the expression $t_1 = t_C + T$ where: $t_C$ is the value set within a range of time points starting from the moment of the aortic valve opening till the moment of the aortic valve closing; T means the transmission time of the pulse wave from the aortic orifice to the compression area. The calculations are carried out in the block 2614. Such a mode provides an antegrade blood flow wave synchronized with R-peak of the current QRS-complex that improves the efficacy of the procedure.

Figure 3:
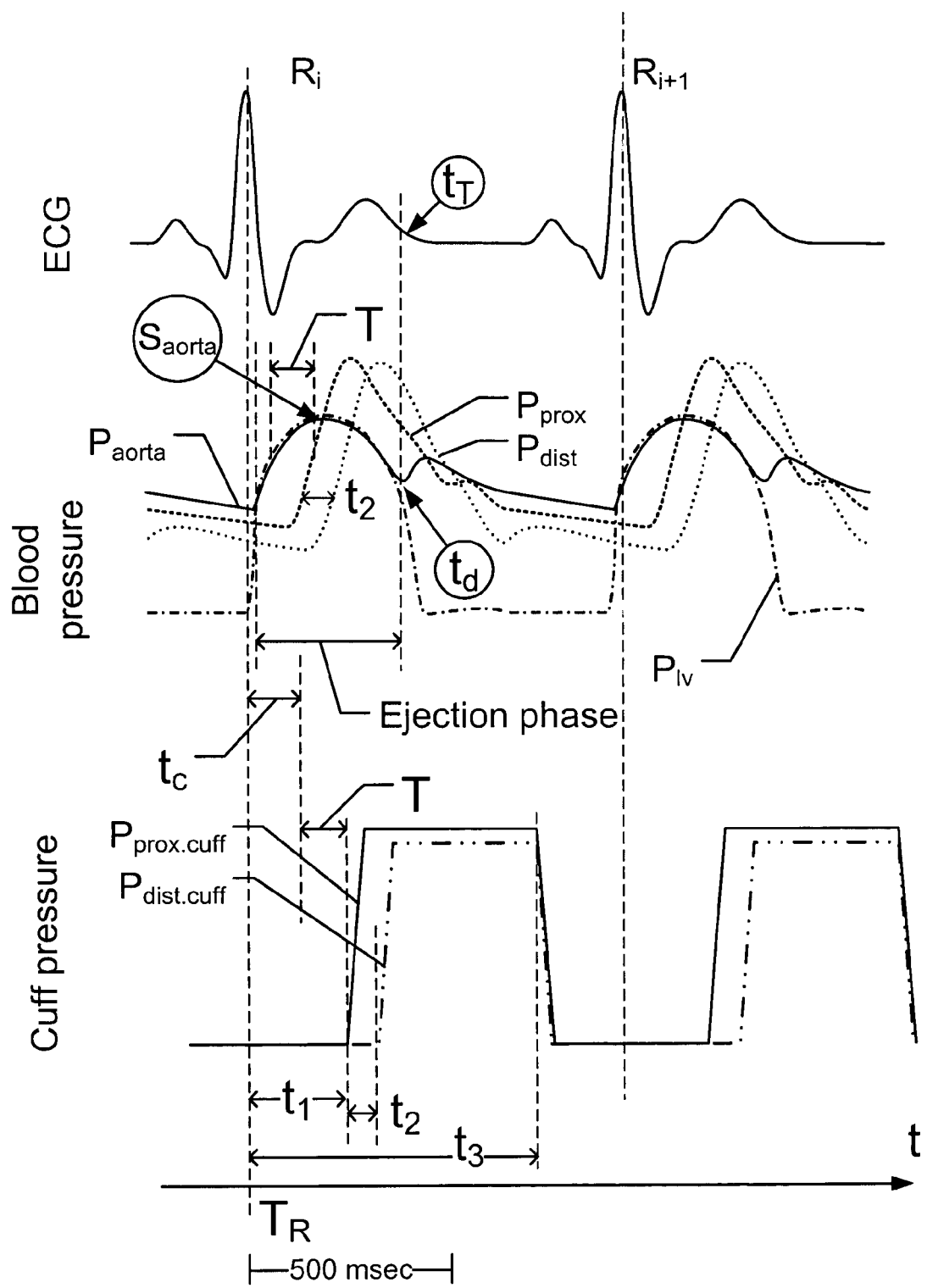
FIG. 3: illustrates a time diagram of modes of the impact on the vessels of extremities.

The physiological basis of the time diagram for generation of pressure impulses in the compression cuffs is explained in FIG. 3. The following is depicted here: the ECG chart, diagrams of systolic pressure in different regions of the cardiovascular system and charts of pressure in the cuffs.

The charts of the blood pressure in different regions of the cardiovascular system shown in FIG. 3 represent approximate pressure dynamics without any effect, and the charts include: blood pressure chart in aorta ($P_{aorta}$), pressure chart in the left ventricle of the heart ($P_{lv}$), blood pressure chart in the region of the proximal cuff ($P_{prox}$) e.g. in the thigh, blood pressure chart in the distal cuff ($P_{dist}$) e.g. over the calf.

An increase of pressure in the aorta during systole is associated with the ejection phase, the beginning of which is approximately 30 to 60 msec after the R-peak of ECG.

The end of ejection phase is associated with the closing of the aortic valve (time point $t_d$). Then isovolumic relaxation starts for around 50 msec, and is followed by diastole. The ending of ejection phase and the beginning of diastolic phase corresponds approximately to the time of expiration of a T-wave on the ECG chart and commonly continues for 270 to 400 msec following the R-peak that mainly depends on the heart rate. The maximum value of pressure in aorta is seen during the ejection phase, 200 to 300 msec after the R-peak on the ECG (time point $S_{aorta}$).

Thus, during the period that includes the ejection following the R-peak on ECG, a pulse wave generates in aorta and it spreads from the heart in the antegrade direction. Its velocity in aorta and major arteries is approximately from 4 to 7 m per sec. The natural pulse wave spreads from the heart to the proximal area of compression e.g. to the thigh during the time T that lasts approximately from 70 to 100 msec.

The curve of pressure in the area of proximal cuffs location $P_{prox}$ resembles the curve of pressure in the aorta $P_{aorta}$ with adding the T value delay for the transmission time of the pulse wave.

Compression of the proximal area and the arteries in the area of the proximal cuffs location leads to an appearance of pressure waves at higher and lower levels regarding the compression area because of the ejection of blood from the compressed arteries.

It is evident that, in order to reinforce the antegrade wave to a maximum extent, it is necessary to produce such superposition of the naturally occurring pulse wave and the wave generated by compression beneath the proximal and distal cuffs, so that the beginning of cuff inflation and, respectively, tissue compression would correspond to the periods of transmission of the natural pulse wave to the location of cuffs.

The time of the transmission is equal to the time of the ejection phase delayed by the time of transmission of a natural pulse wave from the aorta orifice to the area of compression.

The pressure diagrams $P_{prox.cuff}$ and $P_{dist.cuff}$ in the proximal and distal cuffs, respectively, are impulses that begin after the delay $t_1$ and $t_1 + t_2$ following the time of the R-peak, respectively.

The delay $t_1$ that concerns the onset of compression in the proximal cuffs required for achieving the maximum reinforcement of the antegrade wave is approximately equal to the sum of timepoints of the maximum pressure ($S_{aorta}$) and time T of transmission of the pulse wave from the aorta to the mentioned location and, commonly, is in average from 270 to 370 msec. Taking into account a practically executable duration of the inflation front for compression cuffs, the time $t_1$, which represents generation of the compression impulse actually may start even 50 to 100 msec earlier lasting from 170 to 320 msec.

Moreover, compression of the proximal area is associated with an appearance of retrograde pressure wave which is added to the naturally occurring wave including the aortic segment. To prevent a premature closure of the aortic valve and an excessive load applied to the left ventricle caused by the wave, it should reach the aortic orifice not earlier than the time $t_d$. Accordingly, the time of compression onset should be greater than $t_d - T$.

Fulfillment of the condition allows the retrograde pressure wave to reach the aortic orifice during the diastole phase producing useful haemodynamic physiological effects, which are similar to those seen at performing the external counterpulsation.

A practical realization of this condition may be achieved by the ECG analysis and determining the time of ending the T-wave that approximately matches the $t_d$ time point.

The beginning of the pressure impulse in the distal cuff is delayed in relation to the proximal one by the time $t_2$ of pulse wave transmission between the cuffs that is about 30 to 60 msec if the pair thigh-calf is used.

Figure 5:
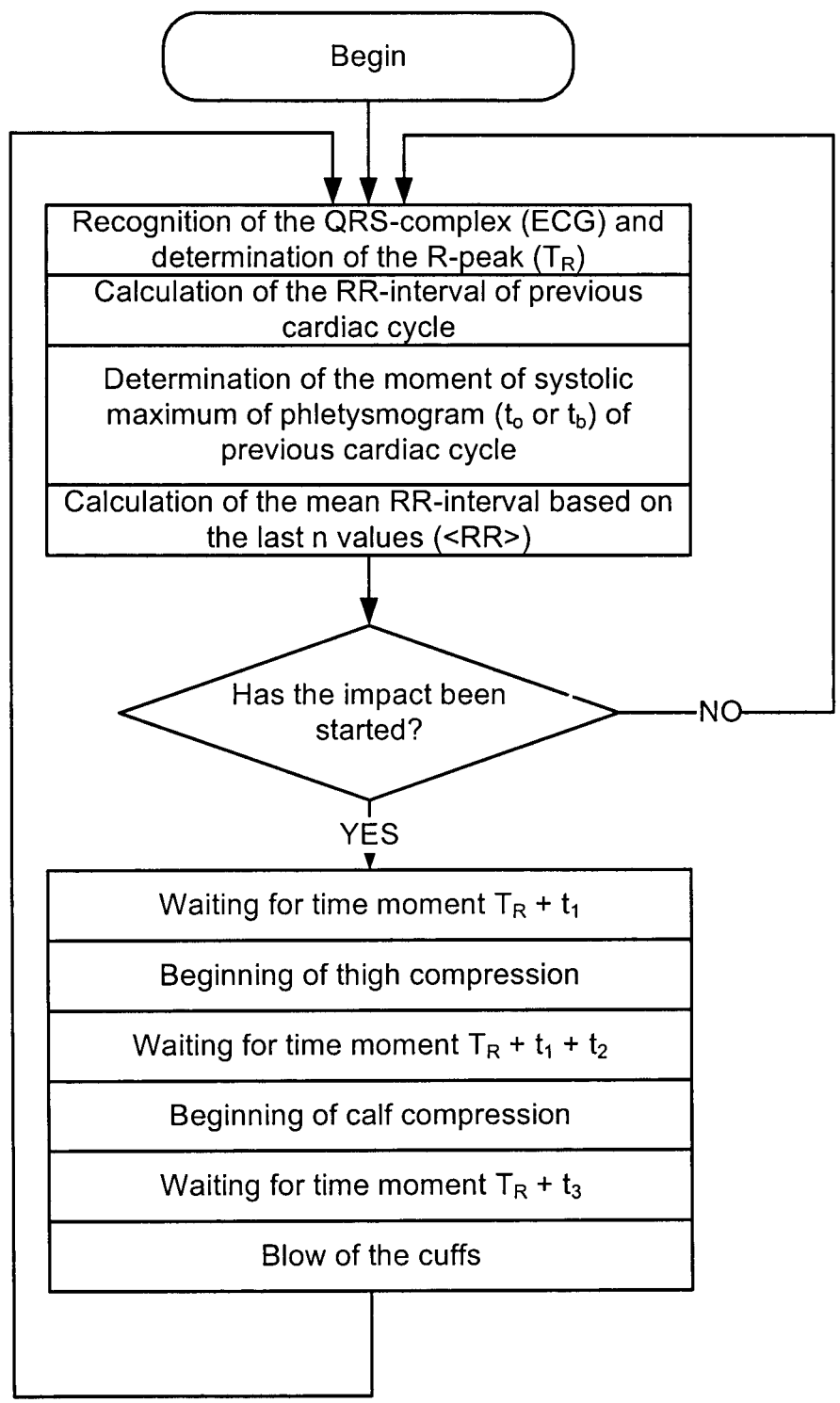
FIG. 5: illustrates an algorithm of generation of time characteristics of the pressure impulses in the cuffs.

The operation algorithm of the unit 2614 used for synchronization and control of the time characteristics of the compression impulses is depicted on FIG. 5 according to designations provided in the cyclogram of FIG. 3.

Figure 4:
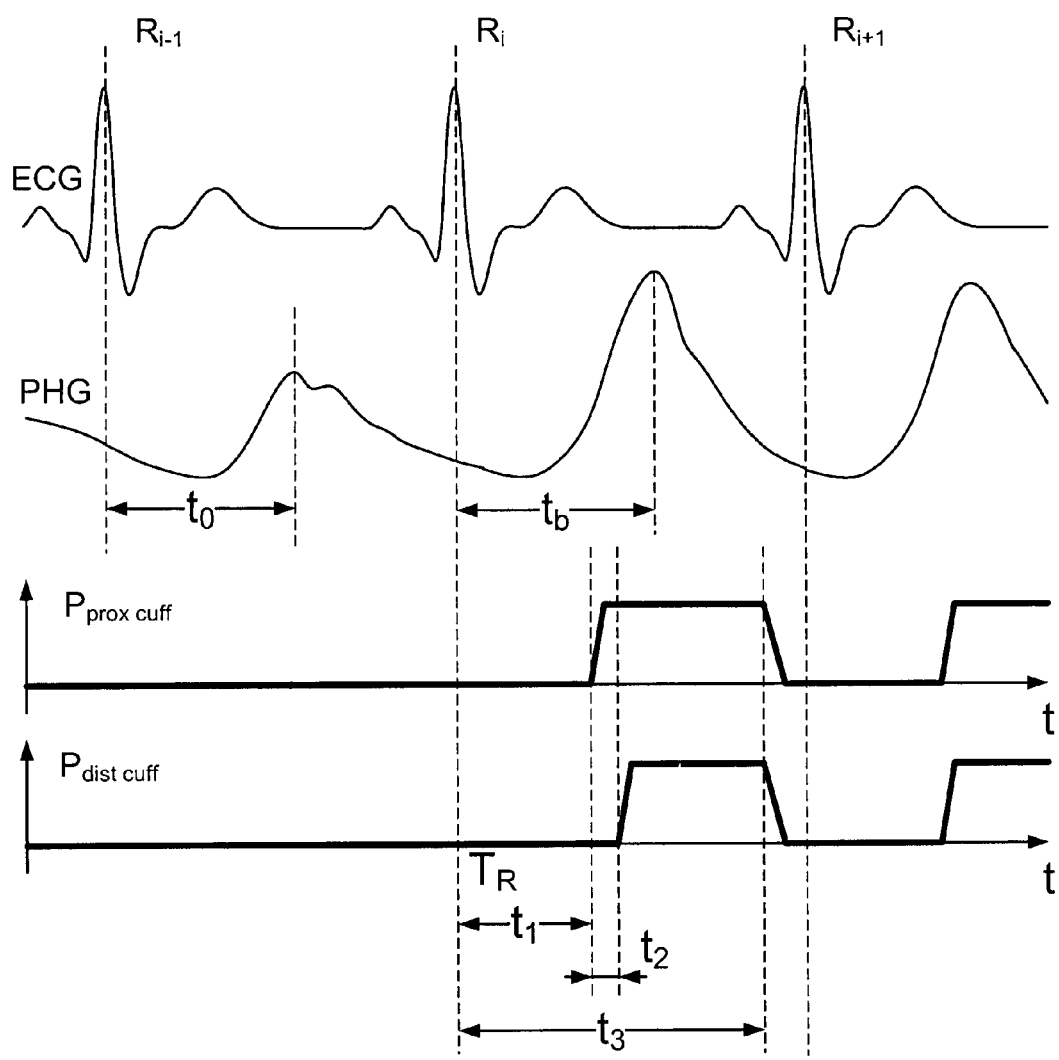
FIG. 4: illustrates a time diagram for explanation of the algorithm of corrections for pressure impulse delays.
Figure 6:
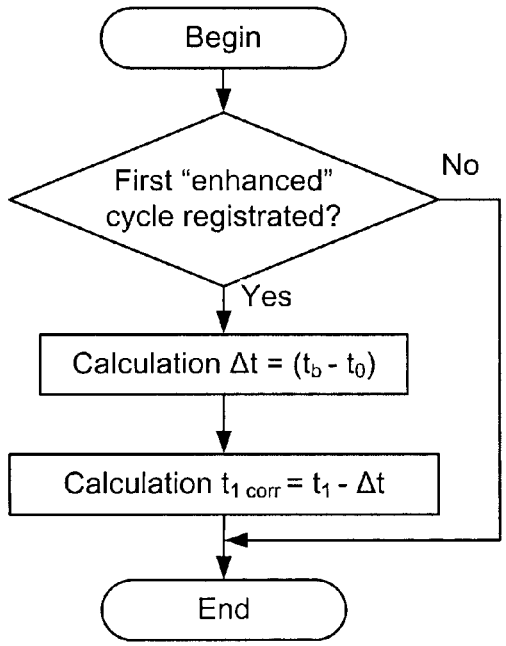
FIG. 6: illustrates an algorithm of adjustment of the delay time for pressure impulses.

Furthermore, optimization of the delay $t_1$ and $t_1+t_2$ following the time of the R-peak used for the onset of compression to the proximal and distal areas, respectively, may be performed as follows (see FIGS. 4,6):

Performing a registration of the blood flow with the use of sensors 31 (or 311) in the areas distal to the area of compression (e.g. distal to cuffs 171 and/or 174), it is recommended to carry out this at the level of a finger or toe defining the delay between the R-peaks of the current QRS-complex and the maximums of the pulse wave both in the absence and in the presence of pressure impulses. Then, the difference of the times $\Delta t$ according to the expression $\Delta t = t_b - t_O$ in the unit 2614 is calculated, where: $t_b$, $t_O$ are the delays between R-peaks and the maximums of the pulse wave in the presence and in the absence of pressure impulses, respectively.

At that, the onset of pressure impulse in the proximal area (cuffs 172 and/or 175) is corrected with the use of the expression: $t_{1\ corr} = t_1 - \Delta t$. Such a correction of the time delay allows taking into consideration the actual time of wave transmission to the area of compression of the pulse wave produced by a cardiac contraction, and performing a correction of the onset of compression for achieving the maximum reinforcement of the resultant wave.

Sending the pressure impulses in the areas of compression is stopped before an initiation of the next QRS-complex, mainly from 0.02 to 0.1 sec prior to it. It allows providing an additional heart unloading as well as a prevention of any decrease of the amplitude of the antegrade blood flow wave.

The claimed method realized with the use of the inventive device is effective even in the case of arrhythmia which may occur during the procedure. To achieve the goal, the onset of the following QRS-complex is calculated in the unit 2614 based on the following expression: $t(QRS_{i+1}) = t(QRS_i) + \langle RR \rangle$, where $t(QRS_i)$ and $t(QRS_{i+1})$ are the onset of the current and the following QRS-complexes, respectively; $\langle RR \rangle = \langle t(QRS_i) - t(QRS_{i-1}) \rangle$ is the mean duration of the cardiac cycle calculated on the basis of several previous cardiac contractions (from 4 to 10 contractions in a real situation).

To control the efficacy of the periodical compression procedure it is convenient to use thermometry: it is necessary to register any local change of temperature, e.g. using a thermistor placed over a finger of the affected extremity or using a contactless measuring equipment and analysis of spatial temperature distribution with a computer-assisted temperature recorder. A means for registration of tissue oxygen saturation in the peripheral area of the affected extremity also can be used. The mentioned methods allow to optimize the impact, to assess physiological changes in the extremities being impacted and to correct the duration of the procedure.

The recommended treatment cycle with the use of the method claimed is as follows: the session duration is from 40 to 60 min every other day, totally from 7 to 10 sessions. It is appropriate to conduct from two to three treatment cycles per year.

Generation of pressure impulses by the gas distribution units 16 in the cuffs 17 is described below by example of functioning of the claimed device in the mode of external counterpulsation. Managing the distributors 161 to 164 (see FIG. 8) (components of the unit 16), which function in the mode of generation of the antegrade wave, is the same.

b) Functioning in the Mode of External Counterpulsation:

In the mode of external counterpulsation, the compression cuff 173 is attached to buttocks, the compression cuffs 172 are attached to the thighs, and the compression cuffs 171 are attached to the calves; all the cuffs are connected to the corresponding gas-distribution units 16 (see FIG. 2,*f*).

The source 18 of high pressure for generation of controlling pressure (~150 Kpa) is switched on; it is followed by switching on the compression air source 10. Within the time of growth of pressure in the receiver 12, while the distributor 161 is closed, impulses of controlling pressure for locking the valve 165 are generated with the distributor 162. During the same period, while the distributor 163 is closed, to connect the cuffs 171 to 173 to the receiver 20 via the valve 167, the distributor 164 connects the control input of the valve 167 to the receiver 20.

Figure 9:
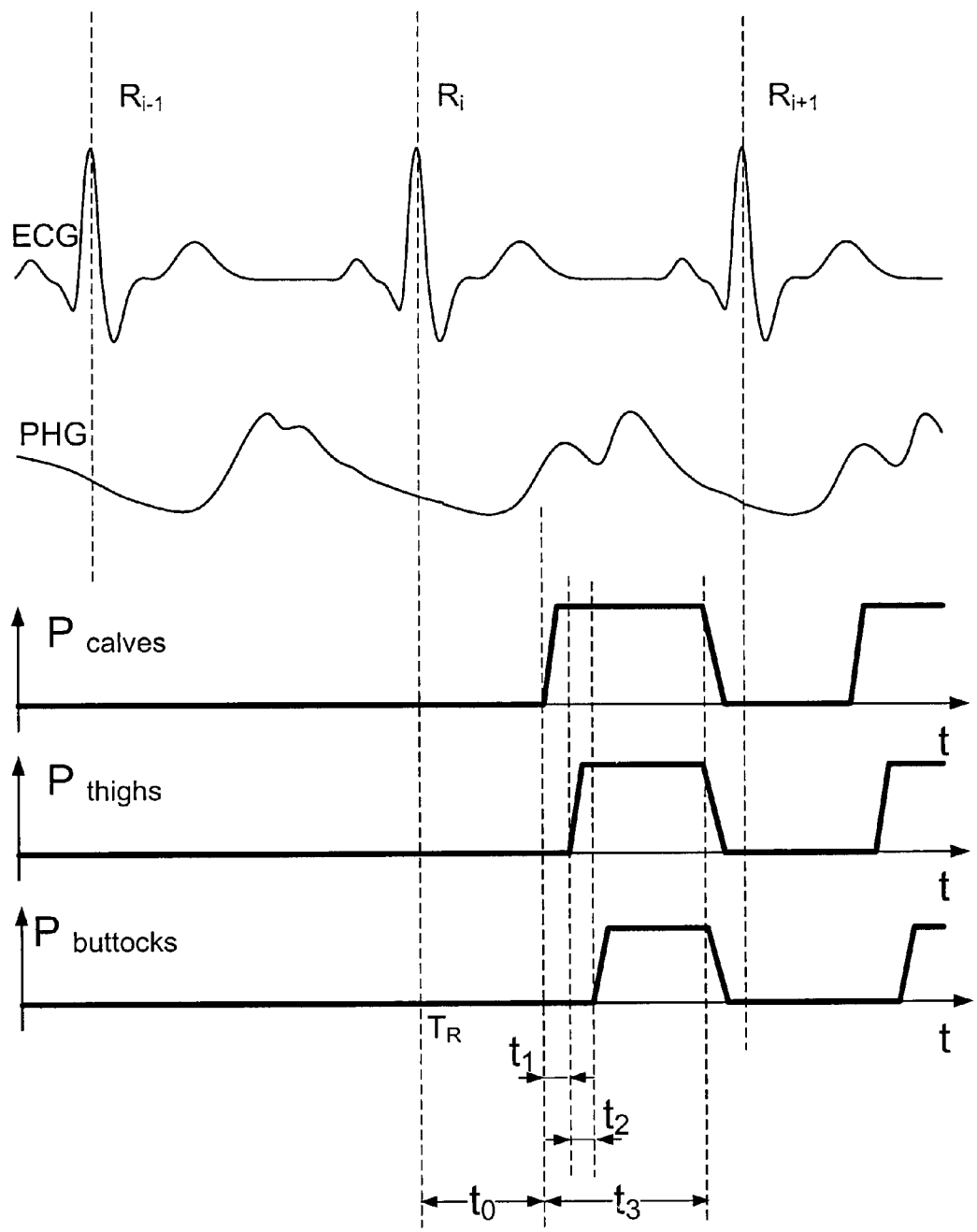
FIG. 9: illustrates a time diagram of generation of pressure impulses in the mode of external counterpulsation.
Figure 10:
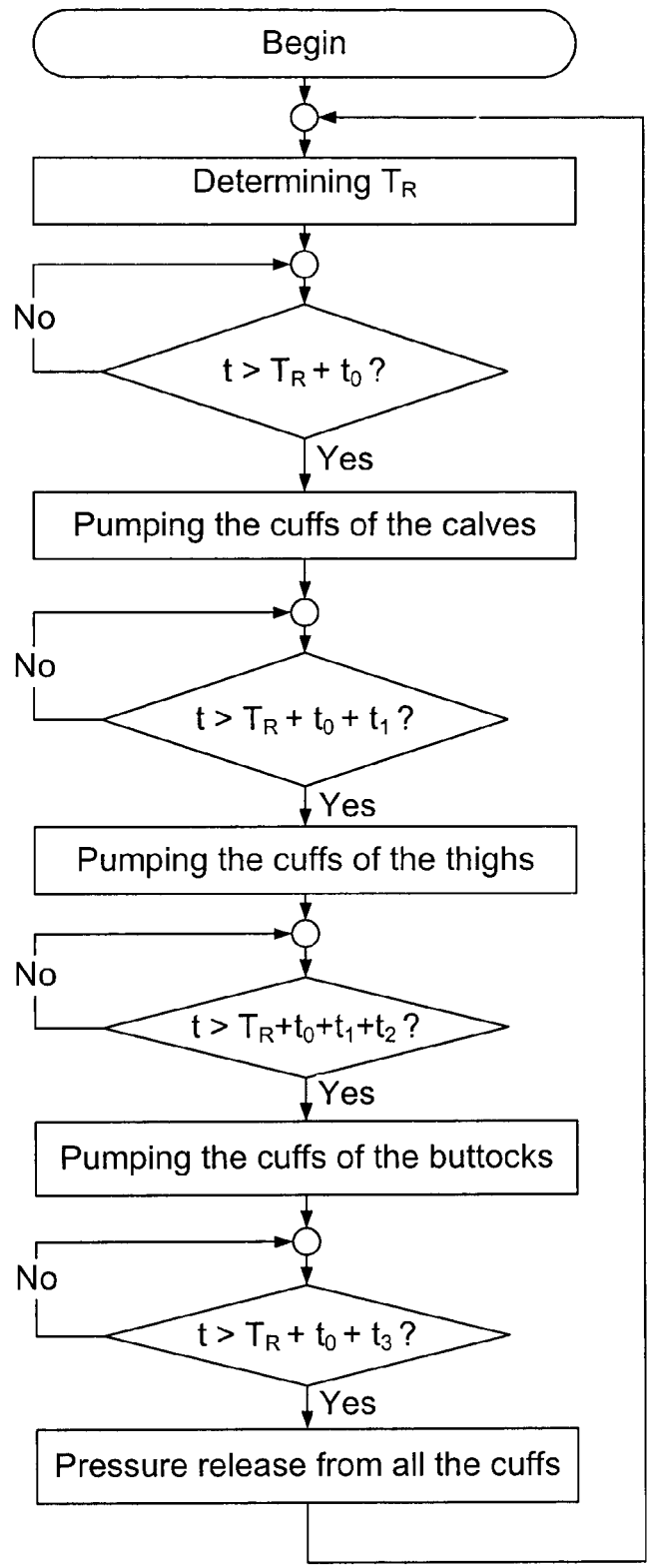
FIG. 10: illustrates an algorithm used for external counterpulsation.

As a working level of pressure in the receiver 12 is achieved, the device (according to the time diagram, FIG. 9) enables the operation algorithm (FIG. 10).

The unit 28 uses the signals received from the unit 2611, which analyses the ECG for determining the time point $T_R$ of the current R-peak on the ECG. As the set delay time $t_0$ has elapsed, the unit 26 generates the controlling signals for inflation of the distal cuffs, e.g. cuffs 171, over the calf. Then, as the delay time $t_1$ after inflating the calf cuff 171 is run, the unit 26 generates controlling signals for inflation of the more proximal cuffs 172, located on the thigh. As the delay time $t_2$ since the time point of pressure pumping into the cuffs 172, placed on the thighs, has elapsed, the unit 26 generates controlling signals for pumping pressure into the more proximal cuff 173 placed on the buttock. After elapsing the time interval $t_3$ since the time following air pumping into the cuff 171, the unit 26 generates controlling signals for simultaneous pressure release from all of the cuffs 171 to 173.

Figure 8:
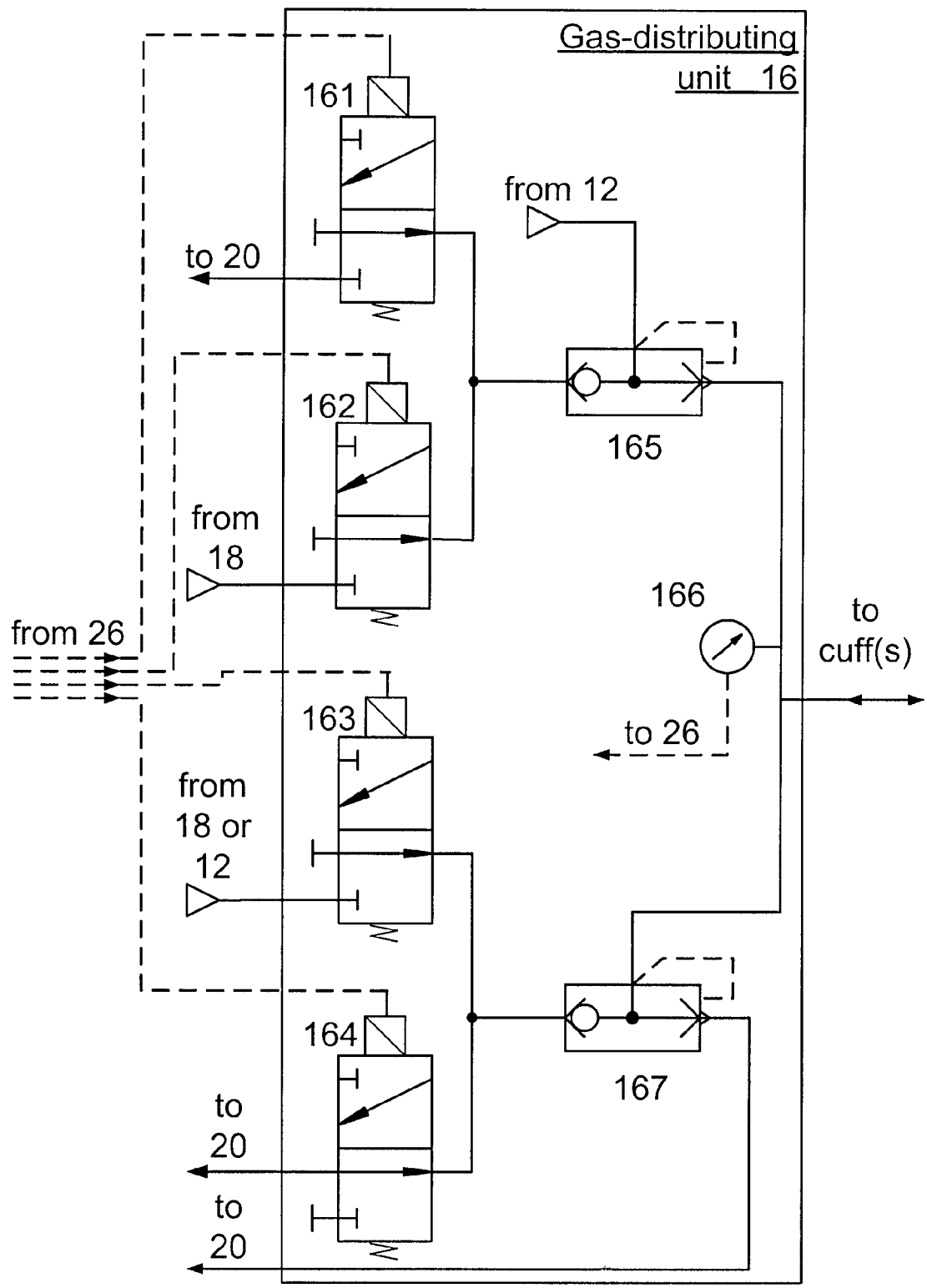
FIG. 8: illustrates a block diagram of the gas-distribution unit.

Generation of the pressure impulse in a specific compression cuff 17 is provided as follows (see FIG. 8).

To disconnect a cuff from the negative pressure receiver 20, the distributor 164 is fed with a control voltage, which switches off the control input of the valve 167 from the receiver 20, and then the distributor 163 is fed with a required voltage. At that, the pressure from the source 18 or from the receiver 12 is passed to the control input of valve 167, and it disconnects the cuffs from the negative pressure receiver 20.

After that, the distributor 161 is fed with a short impulse (approximately 30 msec) of control voltage from the unit 26 that, at this time, connects the control input of valve 165 with the negative pressure receiver 20, or with the environment and releases the locking pressure. The valve 165 is opened, and the compressed air passes from the receiver 12 into a cuff. For cessation of air delivery into the cuff 17, a short impulse (duration approximately 15 msec) is transmitted from the unit 26 to the distributor 162. The distributor 162 is opened that creates the locking pressure at the control input of the valve 165.

The process of pumping pressure into a cuff is controlled by the unit 26 on the basis of feedback signals from the cuff pressure sensor 166. At the end of air injection, the gas-distributing device 16 switches to the mode of supporting pressure in a cuff, the level of which pressure should be guaranteed till the moment of pressure release. At that, the cuff becomes disconnected from the receiver 12 as well as from the receiver 20.

To release the pressure, the distributor 164 is opened that connects the control input of valve 167 to the receiver 20. The valve 167 is opened, and the air passes from the cuff into the receiver 20.

The negative pressure in the receiver 20 allows decreasing the time required to release an excessive pressure from the cuffs (to shorten the duration of the falling edge of the compression impulse) that is important for improving the efficacy of the impact on the cardiovascular system.

The valve 22 for quick pressure release, designed, for instance, in the form of an inverse valve, provides an additional decrease of the excessive pressure release time in the cuffs at the moment of their connection to the receiver 20, as it adds an additional way for release of a positive pressure from the cuffs. Furthermore, it provides a pressure release from the pneumatic system of the device after the finishing of its work.

Such a condition of the gas-distributing device 16 is kept till the moment of onset of generation of the next compression impulse:

(a) the control input of the valve 165 is disconnected by the distributor 161 from the receiver 20 of negative pressure or from the environment, and disconnected by the distributor 162 from the source 18 of high pressure; and (b) the control input of the valve 167 is disconnected by the distributor 163 from the high pressure source 18 or the receiver 12, and is connected by the distributor 164 to the receiver 20 of negative pressure.

As a result, the cuffs become disconnected by the valve 165 from the receiver 12 and become connected to the receiver 20 by the valve 167.

The device for the impact on the cardiovascular system is more universal in terms of regulation (control) and the use of physiological reactions of the cardiovascular system of a patient. The regulation is carried out by adjustment of amplitude-time parameters of the compression impulses using plethysmographic signals from the sensors 31 as the feedback. In addition, using the cardiac rate control, the unit 26, in the manual mode or automatically, stops the impact procedure if any current parameter exceeds predetermined limits of the cardiac contractions. To extend the range of intensity of the impact on the cardiovascular system, it is reasonable to apply the impact not in every cardiac cycle. Thus, the device allows for generating pressure impulses into the compression cuffs 17 with omissions, so that a ratio of the number of compression cycles to the amount of cardiac cycles would range from 1/1 to 1/4.

During the procedure of generation of the impact on the cardiovascular system, particularly, in the mode of external counterpulsation, the upper control circuit of the unit 26 provides the processing of cardiac rhythm parameters, processing of the statistical, geometrical, correlational and frequency parameters of the cardiac rhythm, as well as calculation of an integrating index of the activity of the regulatory systems (TARS) of a patient.

The above described operations are conducted according to methodological recommendations prepared under the decision of the Clinical and Diagnostic Instruments and Devices Board of the Committee of New Medical devices of the Department of public health of Russian Federation (report No. 4 dated Apr. 11, 2000).

The processing can be accomplished for obtaining diagnostic data that concerns the procedure impact on the cardiovascular system.

Figure 7:
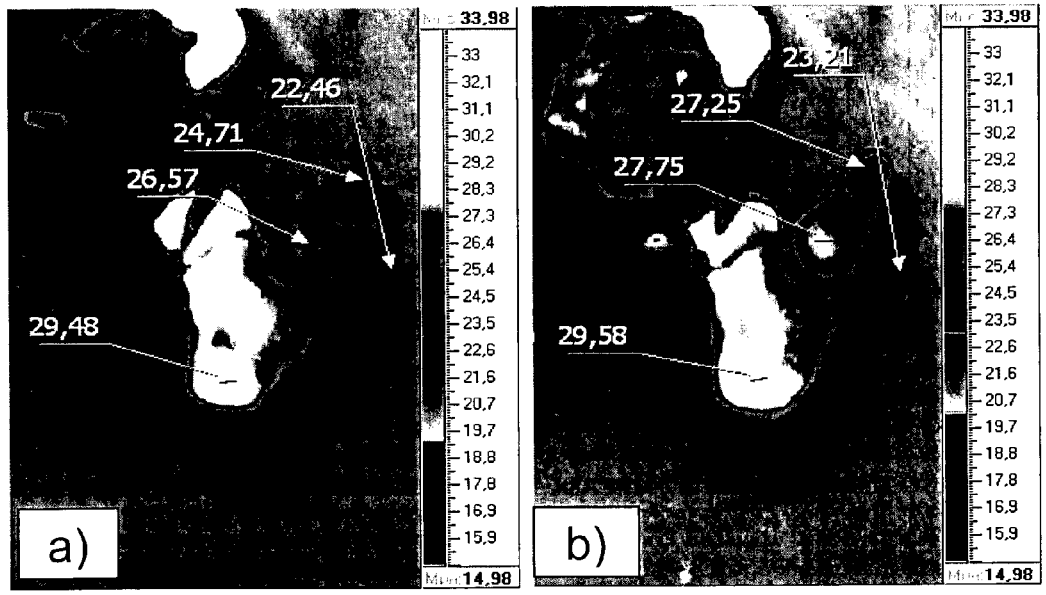
FIG. 7: (a), (b) demonstrate thermograms: before (a) and after (b) the impact on the vessels of the limbs.

The therapeutic effect of the claimed method is confirmed by its clinical use as well as by thermograms certifying the efficacy of the method; these are shown in FIG. 7. Thermographic changes in the lower extremities were registered with the use of the computer-assisted recording thermometer IRTIS-2000 (www.irtis.ru). There is a temperature scale on the right hand side; numerical marks show the values of temperature in the affected areas.

Clinical Case:

Patient N., 56 years-old. He complained of pain in legs for the last 1.5 to 2 years. Pain in the gastrocnemius muscles, intermittent claudication after 300 to 400 m of walking on a flat surface with equal loads 2 steps per second. The patient noted a progression of the disease for the last year. He received two courses of treatment with infusions of Vasoprostan; a positive effect for the next 2 to 3 months, following the treatment, was achieved.

At physical examination: ABP: on the humeral artery 120/88 mm Hg; on the right foot 65 mm Hg, on the left foot 65 mm Hg. Ankle brachial index (ABI): 0.54 on the left side and 0.54 on the right side.

The patient underwent duplex ultrasonography screening of the arteries of the lower extremities. Conclusion: stenosis of the right common femoral artery is 22%; stenosis of the left common femoral artery is 52%. Occlusion of the anterior femoral arteries bilateral at the level of the Gunther's channel. Occlusion of the anterior tibial artery on the right side.

Diagnosis: Chronic obliterating disease of the arteries of the lower extremities, 2B stage according to Fontaine-Pokrovsky.

The patient underwent a course of 10 sessions of the patent-pending method of experimental treatment for the disease of the lower extremities. Duration of each session was 50 minutes. Compression cuffs were placed over the middle part of the thighs and upper third of calves. The pressure impulse in the femoral cuffs was generated with the delay 200±50 msec after the R-peak on the ECG. The pressure impulse in shin cuffs was generated with the delay 50 msec after the beginning of action in the femoral cuffs. Amplitude of the pressure in the cuffs was set by 20 to 40 mm Hg higher than the level of the current arterial blood pressure. For a prompt control of the blood flow, a finger/toe sensor was placed for plethysmogram registration. Changes of the temperature in the lower extremities were registered with the use of computer-assisted recording thermometer (see FIG. 7). Comparing to the initial condition (FIG. 7, a) there is an increase of temperature in the foot of the affected extremity (mean increment consisted 1 to 3° C.) (FIG. 7, b) that indicates improvement of the blood flow in the distal area.

During the therapeutic session, the amplitude of arterial pulsation in the lower extremity registered by the plethysmographic sensor is characterized by 5- to 7-fold increase.

Right after the first treatment session, the patient noted 'lightness' in his legs and significant pain relief at walk. After the completion of the treatment course, the patient was able to walk for 1.5 to 2 km with no difficulties; the syndrome of intermittent claudication was absent. There was observed an obvious conversion of the disease into another functional class, Class 1-2A, according to the classification of Fontaine-Pokrovsky. After the 10th session of the treatment, ABP in the foot arteries increased up to 85 mm Hg that was obviously associated with a significant improvement of collateral arterial communications. The ABI increased up to 0.7 bilaterally.

INDUSTRIAL APPLICABILITY

Means and components that provide the generation and control of pressure impulses in the cuffs may be designed based on the modern hardware components of pneumatic automation and in the way that it is implemented in the devices "CARDIOPULSAR"® (www.constel.ru) for supplementary blood circulation with the use of the method of external counterpulsation.

The invention claimed is:

1. A method for producing an impact on the cardiovascular system of a human characterized with a blood flow and a blood pressure pulse wave having predetermined blood pressure pulse parameters, said method comprising the steps of:
providing an electrocardiogram (ECG) with a current ORS-complex, including an R-wave;
providing a periodical compression of the human's extremities within a proximal zone, located at a predetermined distance downstream from the human's heart, and within a distal zone located downstream from the human's heart further than the proximal zone; said compression is provided by means of a plurality of pressure impulses, characterized with predetermined impulse parameters, each said pressure impulse is characterized with a front of the impulse; and said pressure impulses are synchronized with said QRS-complex and according to said blood pressure pulse parameters;
providing a registration of the blood flow performed at a point located downstream from the human's heart further than said distal zone;
providing a correction of the impulse parameters on the basis of said registration of the blood flow;
wherein:
the periodical compression of each said extremity is performed separately within said distal zone and said proximal zone, and said pressure impulses are delivered to said distal zone and to said proximal zone with a delay relatively to each other; said delay is provided as follows:
the front of the pressure impulse within the proximal zone is delayed in relation to the R-wave of the current QRS complex so that the pressure impulse in the proximal zone starts at the time of passing the blood pressure pulse wave from the human's heart through said proximal zone;
the front of the pressure impulse within the distal zone is delayed in relation to the front of the pressure impulse in the proximal zone for the time of passing the blood pressure pulse wave between said proximal zone and said distal zone;
wherein the compression within the said proximal and distal zones is terminated simultaneously prior to the start of a next QRS complex following the current QRS complex; and
wherein said registration of the blood flow is performed on the human's finger or toe;
delays between R-waves of the current QRS-complex and the maximums of the blood pressure pulse waves in the absence and in the presence of said pressure impulses are determined; a difference $\Delta t$ is calculated according to the expression of:

$\Delta t = t_b - t_O$, wherein:

$t_b$, $t_O$ are the delays between R-peaks and the maximum values of the blood pressure pulse wave in the presence or in the absence of said pressure impulses, respectively; and the front of the pressure impulse $t_1$ in the said proximal zone is corrected according with the following expression: $T_{1\ corr.} = t_1 - \Delta t$.

2. A device for producing an impact on the cardiovascular system of a patient characterized with a current QRS-complex of ECG; said device comprising:
a source of compressed air;
a plurality of gas-distribution units;
each said gas-distribution unit includes two pneumatic mechanical quick exhaust air valves each having input control Ports and output ports, four electromechanical distributors, and a pressure sensor;
a receiver connected to said source of compressed air;
a source of high pressure connected with said plurality of gas-distribution units;
a control and indication unit connected to said plurality of gas-distribution units;
an analyzer of the current QRS-complex, said analyzer is associated with said control and indication unit;
a unit for plethysmographic registration associated with the control and indication unit;
a receiver of negative pressure connected to said source of compressed air, and to said plurality of gas-distribution units;
a plurality of compression cuffs, applied over the patient's body and connected to said source of compressed air via said gas-distribution units and via said receiver;
wherein: in each said gas-distribution unit, said input control ports are associated, via said electromechanical distributors, with said source of high pressure; said output port of one of the two pneumatic mechanical quick exhaust air valves is associated with the corresponding compression cuff, and said output port of the other of the two pneumatic mechanical quick exhaust air valves is associated with the receiver of negative pressure.

3. The device according to claim 2, further comprising: a blood pressure gauge associated with said control and indication unit and capable of correcting the pressure in said compression cuffs depending on a current value of the patient's blood pressure.

4. The device according to claim 2, further comprising a heart rate gauge connected to said control and indication unit capable of terminating the impact, if the patient's current heart rate is out of predetermined limits.

5. The device according to claim 2, wherein said receiver of negative pressure is equipped with a quick pressure release valve and a non-reverse valve communicating the receiver to the environment.

6. The device according to claim 2, wherein said control and indication unit comprises an upper level control circuit and a lower level control circuit; said upper level control circuit is designed based on a personal computer capable of analyzing the patient's physiological signals reflecting the patient's condition, and capable of generation of control commands for said lower control circuit; said lower level control circuit is designed based on a microprocessor controller for generation of control signals for said plurality of gas-distribution units.

7. The device according to claim 2, wherein said current QRS-complex includes an R-wave; and
said control and indication unit is capable of regulation of a delay of pumping the pressure into said compression cuffs in relation to the R-wave.

8. The device according to claim 2, wherein said control and indication unit is capable of setting a delay of starting the pressure pumping in each said compression cuff positioned proximally downstream from the patient's heart in relation to the respective compression cuff positioned distally downstream from the patient's heart.

9. The device according to claim 2, wherein said current QRS-complex includes an R-wave; and
   said control and indication unit is capable of changing a delay of starting the pressure pumping in the compression cuffs in relation to the R-wave depending on signals received from said unit for plethysmographic registration.

10. The device according to claim 2, wherein the said control and indication unit provides for a ratio of a number of compression cycles in said compression cuffs to a number of QRS complex cycles ranging from 1/1 to 1/4.

11. The device according to claim 2, wherein
    said plurality of compression cuffs are represented by two pairs of cuffs being respectively femoral and calf cuffs for each lower extremity of the patient, connected correspondingly to said gas-distributing units in parallel.

12. The device according to claim 2, wherein
    said plurality of compression cuffs are represented by two pairs of cuffs, being respectively arm and forearm cuffs for each extremity of the patient, connected correspondingly to said gas-distributing units in parallel.

13. The device according to claim 2, wherein
    said plurality of compression cuffs are represented by four pairs of cuffs, being respectively arm, forearm, femoral, and calf cuffs for each respective extremity, connected correspondingly to said gas-distributing units in parallel.

* * * * *